United States Patent [19]
Venkatraman et al.

[11] Patent Number: 5,246,705
[45] Date of Patent: Sep. 21, 1993

[54] OCCLUSIVE, ELASTOMERIC BACKING MATERIALS IN TRANSDERMAL DRUG DELIVERY SYSTEMS, AND ASSOCIATED METHODS OF MANUFACTURE AND USE

[75] Inventors: Subbu S. Venkatraman, Palo Alto; Scott E. Smith, San Mateo, both of Calif.

[73] Assignee: Cygnus Therapeutic System, Redwood City, Calif.

[21] Appl. No.: 865,140

[22] Filed: Apr. 8, 1992

[51] Int. Cl.$^5$ .............................. A61F 13/02
[52] U.S. Cl. .................... 424/448; 424/447; 424/449; 428/343; 428/355; 602/52; 602/54; 602/57; 602/58
[58] Field of Search ............ 424/448, 449, 447; 428/343, 355; 602/52, 54, 57, 58

[56] References Cited

U.S. PATENT DOCUMENTS

| | | | |
|---|---|---|---|
| 3,645,835 | 2/1972 | Hodgson | 161/146 |
| 4,655,768 | 4/1987 | Marecki | 604/897 |
| 4,725,439 | 2/1988 | Campbell et al. | 424/449 |
| 4,867,982 | 9/1989 | Campbell et al. | 424/449 |
| 4,906,463 | 3/1990 | Cleary et al. | 424/78 |
| 4,911,916 | 3/1990 | Cleary | 424/449 |
| 4,917,929 | 4/1990 | Heinecke | 428/41 |
| 4,942,037 | 7/1990 | Bondi et al. | 424/448 |
| 4,987,893 | 1/1991 | Salamone | 128/156 |
| 5,006,342 | 4/1991 | Cleary et al. | 424/445 |
| 5,012,801 | 5/1991 | Feret | 128/155 |
| 5,032,403 | 7/1991 | Sinnreich | 424/448 |

Primary Examiner—Thurman K. Page
Assistant Examiner—D. Gabrielle Phelan
Attorney, Agent, or Firm—Morrison & Foerster

[57] ABSTRACT

Improved transdermal drug delivery systems are provided which contain an occlusive, elastomeric backing layer which is preferably liquid-resistant. The systems contain as a backing layer a single homogeneous sheet of an elastomeric material having a moisture vapor transmission rate ("MVTR") in the range of about 0.1 to 20 g/m$^2$/hr and a Young's modulus in the range of about $10^4$ to $10^9$ dynes/cm$^2$. Methods for making and using transdermal drug delivery devices containing such backing layers are provided as well.

18 Claims, No Drawings

OCCLUSIVE, ELASTOMERIC BACKING MATERIALS IN TRANSDERMAL DRUG DELIVERY SYSTEMS, AND ASSOCIATED METHODS OF MANUFACTURE AND USE

DESCRIPTION

Technical Field

This invention relates generally to transdermal drug delivery systems, and more particularly relates to improved such systems containing an occlusive, elastomeric backing layer. The invention also relates to methods of manufacturing and using such systems.

Background of the Invention

A variety of devices and systems have been proposed for administering drugs transdermally. These devices are generally in the form of a bandage or skin patch that includes: a reservoir which contains the drug; a pressure-sensitive adhesive layer which is permeable to the drug and by which the device is attached to the skin; and a backing layer that is substantially impermeable to the drug and serves as the upper surface of the device during use. Many variations in such devices are possible. For example, the pressure-sensitive adhesive component may itself serve as the drug reservoir, or there may be one or more additional layers in the device, e.g., a membrane to control the release rate of drug and/or skin permeation enhancer, a structurally reinforcing layer to prevent curling or delamination, additional "anchor" adhesive layers, or the like.

The present invention is directed to a novel backing layer for use in such systems. The backing layer comprises a material which is preferably occlusive to water vapor (and thus enhances the transdermal transport of certain drugs), elastomeric in character (and is thus highly useful in patches which are worn for extended periods), and resistant to commonly used liquid vehicles, solvents, enhancers, and the like. Although many types of materials are currently used to fabricate backing layers in transdermal drug delivery systems, applicants are unaware of any art which teaches or suggests the use of the occlusive, elastomeric, and generally liquid-resistant materials disclosed and claimed herein.

OVERVIEW OF RELATED ART

The following references relate to one or more aspects of the present invention.

U.S. Pat. Nos. 4,725,439 and 4,867,982 to Campbell et al. describe a transdermal drug delivery device which is stated to be sufficiently flexible and deformable so as to enable use on sensitive skin areas for extended periods of time.

U.S. Pat. Nos. 4,906,463 and 5,006,342 to Cleary et al. describe a transdermal drug delivery device containing a multiplicity of spaced apart structural laminae which provide the device with resiliency and firmness.

U.S. Pat. No. 4,911,916 to Cleary describes a resilient laminated composite which includes an upper layer of a resilient elastomer, an intermediate diffusion matrix layer of a polyurethane macroporous foam containing drug and polysiloxane adhesive, and a basal surface layer of adhesive.

U.S. Pat. No. 4,942,037 to Bondi et al. describes the use of vinyl acetate-vinyl chloride copolymers, polyethylene terephthalate, polyethylene, polyvinylidene chloride, polyester and other materials as the backing layer. Bondi et al. note that the material to be used as the backing layer should have "the properties of impermeability to the drug and strength and flexibility as a support."

DISCLOSURE OF THE INVENTION

One aspect of the invention is an improved transdermal drug delivery device for administering a drug to a predetermined area of skin or mucosa, comprising a laminated composite which includes (a) a layer of a pressure-sensitive, pharmaceutically acceptable adhesive comprised of a material that is permeable to the drug, and which defines the basal surface of the device and adheres to the skin during use, and (b) a backing layer that is substantially impermeable to the drug and which defines the upper surface of the device during use, wherein the improvement comprises:

employing as the backing layer a single homogeneous sheet of an elastomeric material having a moisture vapor transmission rate ("MVTR") in the range of about 0.1 to 20 $g/m^2/hr$ and a Young's modulus in the range of about $10^4$ to about $10^9$ dynes/$cm^2$, and which is inert with respect to all components of the device.

In another aspect of the invention, an improved method for administering a drug to a predetermined area of skin or mucosa is provided, which comprises placing a drug-containing laminated composite as just described in drug-transmitting relationship to the skin.

In still another aspect of the invention, an improved method is provided for making a transdermal drug delivery device, which comprises laminating a pharmaceutically acceptable, pressure-sensitive adhesive layer to a backing layer as will be described in detail herein.

The backing layer materials which are the focal point of the present invention provide for a number of advantages relative to conventional backing layers. First, because the present materials are occlusive, transdermal transport of certain drugs, e.g., steroids, is enhanced. Second, because the backing layer material is elastomeric, it is suited for fabrication of transdermal systems designed to be worn for extended periods of time, i.e., transdermal systems containing these backing layers may be comfortably worn for at least several days. Additionally, the need for multi-layer backings is obviated. That is, in a number of the patents cited and discussed above, desired properties are achieved only with multi-layer backings; with the present invention, however, the backing material is a single homogeneous layer. As a consequence, the design and manufacture of transdermal devices according to the present invention is considerably simplified. Finally, the materials used herein are preferably resistant to commonly used liquid vehicles, solvents, enhancers, and the like. The present materials will not swell and lose mechanical integrity, nor will they remove liquid excipients and thereby influence transdermal transport.

DETAILED DESCRIPTION OF THE INVENTION

Definitions:

Before describing the present invention in detail, it is to be understood that this invention is not limited to particular drugs or transdermal systems, or to specific backing materials, as described herein, as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a thermoplastic elastomer" includes a mixture of two or more thermoplastic elastomers, reference to "a drug" includes reference to one or more drugs, and the like.

In describing and claiming the present invention, the following terminology will be used in accordance with the definitions set out below.

By "transdermal" delivery, applicants intend to include both transdermal (or "percutaneous") and transmucosal administration, i.e., delivery by passage of a drug through the skin or mucosal tissue and into the bloodstream. The present invention is also useful in conjunction with laminated systems for topical drug delivery, and such is intended to be encompassed by the present disclosure and claims.

By the term "pharmacologically active agent" or "drug" as used herein is meant any chemical material or compound suitable for transdermal or trans mucosal administration which induces a desired systemic effect. Such substances include the broad classes of compounds normally delivered through body surfaces and membranes, including skin. In general, this includes: anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmic; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers.

Preferred drugs to be administered in conjunction with the transdermal systems of the invention are those which typically display a low skin flux, e.g., steroid drugs, calcium channel blockers and potassium channel blockers. Examples of steroid drugs useful herein include: progestogens such as norethindrone, norethindrone acetate, desogestrel, 3-keto desogestrel, gestadene and levonorgestrel; estrogens such as estradiol and its esters, e.g., estradiol valerate, cyprionate, decanoate and acetate, as well as ethinyl estradiol; corticosteroids such as cortisone, hydrocortisone, and fluocinolone acetonide; and testosterone. Calcium channel blockers useful in conjunction with the presently disclosed transdermal systems include: arylalkylamines such as bencyclane, bepridil hydrochloride, caroverine, cetiedil citrate, diltiazem hydrochloride, doprenilamine, etafenone, fendiline, mecinarone, prenylamine, proadifen, and terodiline; phenyldihydropyridine derivatives such as amlodipine, darodipine, felodipine, flordipine, isrodipine, mesudipine, nicardipine, nifedipine, niludipine, nilvadipine, nimodipine, nisoldipine, nitrendipine, oxodipine, and riodipine; piperazine derivatives such as cinnarizine, flunarizine and lidoflazine; verapamil and related drugs such as anipamil, dagapamil, devapamil, emopamil, falipamil, gallopamil, methoxyverapamil, ronipamil, tiapamil, and verapamil hydrochloride; and miscellaneous agents such as fluotnidine, fostedil, perhexiline and piprofurol. Suitable potassium channel blockers include, for example, bimakalin and related drugs.

By "therapeutically effective" amount of a pharmacologically active agent is meant a nontoxic but sufficient amount of a compound to provide the desired therapeutic effect.

The term "polymer" as used herein is intended to include both oligomeric and polymeric materials, i.e., compounds which include two or more monomeric units, and may or may not be cross-linked The polymers useful in conjunction with the present invention are elastomers. The term "elastomer" is used in its conventional sense to mean a material with rubbery properties of high elongation and flexibility, and includes both thermoplastic elastomers and crosslinked elastomers. The term "thermoplastic elastomer" (TPE) as used herein denotes a material having elastomeric properties at room temperature but melts and flows like a conventional thermoplastic material at higher temperatures. Internal crosslinks in the case of thermoplastic elastomers are not permanent covalent crosslinks but are thermally reversible physical junctions. The term "crosslinked elastomer" (CLE) as used herein defines a material that behaves like an elastomer at room temperature, and cannot be melted and reformed at higher temperatures. The crosslinks are permanent covalent bonds, and are usually formed during the cure process. When high-temperature curing is required, these CLEs are also called "thermosetting elastomers".

The backing materials which are the focus of the present invention are comprised of an elastomer which, first of all, has a moisture vapor transmission rate in the range of about 0.1 o 20 g/m$^2$/hr, more particularly 0.1 to 2 g/m$^2$/hr, as measured using an evaporimeter at normal skin temperature (approximately 32° C.) and humidity (approximately 60%) (see Example 1). This is in contrast to the higher MVTR of materials such as polyurethane, polytetrafluoroethylene (e.g., Goretex®, available from W. L. Gore & Associates, Inc., Newark Del.), microporous plastic (e.g., Exxaire®, available from Exxon Corporation, Irving, Tex.), or the like, which are "breathable" or more permeable.

The present backing materials are also elastomeric in nature, having a Young's modulus in the range of about $10^4$ to $10^9$ dynes/cm$^2$, more preferably $10^6$ to $10^8$ dynes/cm$^2$. This ensures that the transdermal device will conform to the skin and be comfortable even when worn for several days or longer.

Finally, the backing materials selected herein are preferably such that they are resistant to commonly used liquid vehicles, solvents, enhancers, and the like, including the enhancers described in applicants' commonly assigned U.S. Pat. No. 5,059,426 to Chiang et al., i.e., they are chemically and physically inert to such liquids. In use, this means that the backing materials will not react in any way with the components of the transdermal drug delivery device, nor will they swell during use, lose mechanical integrity, or remove liquid excipients.

Preferred materials for use as the backing layer herein accordingly comprise elastomers with an MVTR and a Young's modulus as described earlier, and may be either thermoplastic elastomers or crosslinked elastomers.

Suitable thermoplastic elastomers include, for example: an A-B-A block copolymer; a blend of an A-B-A block copolymer with a polyolefin such as polyethylene or polypropylene; a blend of an A-B-A block copolymer with poly(dimethyl siloxane); high molecular weight polyisobutylenes; mixtures of vulcanized polymers in a thermoplastic matrix, for example, the so-called dynamically vulcanized mixtures of ethylene-propylene diene rubber and polypropylene (commercially sold as Santoprene ®) and mixtures of nitrile/-natural rubber with polypropylene (commercially available, for example, as Geolast ®). Particularly preferred are A-B-A block copolymers wherein the A blocks are styrene and the B blocks are saturated hydrocarbons (such as ethylene-butylene, ethylene-propylene, or hydrogenated butadiene), with molecular weights greater than about 100,000 and styrene contents ranging from 10 to 40% (available commercially as Kraton ® G Rubbers from Shell Chemical Company) or blends of such polymers with up to about 15% polyethylene or polypropylene (also available under the name Kraton ® G from Shell Chemical Company) or blends of such polymers with up to 10% poly(dimethyl siloxane) and 15% polypropylene (e.g., that sold as C-Flex ® resin by Concept Polymer Technologies).

Crosslinked elastomers suitable for the backing material include elastomers which are crosslinked by either heat or radiation. Specific examples of such materials include vulcanized natural rubber, vulcanized fluoroelastomers, or copolymers of such compounds with a polyolefin such as polyethylene or polypropylene, and mixtures thereof. Crosslinked elastomers can include, for example: copolymers of vinylidene fluoride (VF2), hexafluoropropylene (HFP), and tetrafluoroethylene (TFE) with cure additives (commercially available as Viton ® from DuPont and as Fluorel ® elastomers from 3M Company), and fully hydrogenated crosslinkable butadiene-acrylonitrile copolymer (available commercially as Therban ® from Mobay Chemical Company).

In certain applications, it may not be necessary that the backing material be resistant to liquids, e.g., when the drug reservoir or other layer adjacent to the backing material does not contain any low molecular weight excipients. In these systems, an additional class of thermoplastic elastomers may be used, including: A-B-A block terpolymers, wherein the A blocks are styrene, and the B blocks are unsaturated hydrocarbons such as, for example, isoprene or butadiene (available as Kraton ® D Resins from Shell Chemical Company); blends of such polymers with polypropylene or polyethylene (also available under the name Kraton ® D from Shell Chemical Company); and nitrile rubbers, such as acrylonitrile-butadiene copolymers with about 30 to 50% acrylonitrile content (e.g., that available as Chemigum ® from Goodyear or Hycar ® from B.F. Goodrich). Certain crosslinked elastomers may also be used in systems which do not require that the backing layer be resistant to liquids, including ethylene-propylene diene rubbers with cure additives (e.g., Vistalon ®, available from Exxon Chemical Co., and Buna APR, available from Huls-America) and mixtures of ethylene-propylene diene rubber with other rubbers, such as nitrile or styrene-butadiene rubbers.

Some of these commercially available backing materials may also include plasticizers such as mineral oil or silicone oil, or pigments. The backing layer will typically be about 1 to 10 mils thick, more preferably about 3 to 6 mils thick.

The backing layers may be incorporated into any one of a number of different types of transdermal drug delivery systems. Such systems will typically include, laminated to the backing layer, a pressure-sensitive, pharmaceutically acceptable adhesive layer which serves as the reservoir for the drug. Such an adhesive layer will be comprised of a material that is permeable to the drug contained therein, and which defines the basal surface of the device. Examples of suitable materials for the adhesive layer include polyethylenes, polysiloxanes, polyisobutylenes, polyacrylates, polyurethanes, plasticized ethylene-vinyl acetate copolymers, low molecular weight polyether block amide copolymers (PEBAX copolymers), tacky rubbers such as polyisobutene, polystyrene-isoprene copolymers, polystyrene-butadiene copolymers, and the like. The backing layers may also be used in transdermal systems wherein the drug and associated carriers, vehicles, or the like, are present in liquid form in a "compartment" of a transdermal system, rather than dispersed in an adhesive matrix. It will be appreciated by those skilled in the art that such systems can include a number of different types of (1) laminae, e.g., for structural reinforcement, as described in commonly assigned U.S. Pat. No. 4,915,950 to Miranda et al., or for controlling the rate of delivery of drug from the device, and (2) chemical compounds, e.g., skin permeation enhancers, carriers, vehicles, solubilizers, opacifiers, preservatives, anti-oxidants, surfactants, and the like.

The elastomeric backing layer of the invention, if comprised of a TPE, may be fabricated by calendering, cast film extrusion or blown-film extrusion. The thermosetting elastomer (TSE) films can be prepared by solution casting followed by heating.

A transdermal system containing the elastomeric backing layer may be prepared as follows. An adhesive containing drug, excipients and the like (which will serve as the drug reservoir) is cast onto a release liner. Solvent is evaporated therefrom, and the adhesive is then transfer-laminated onto the backing film. Alternatively, the adhesive solution may be cast directly onto the backing layer and heated at a temperature of at least about 50° C. below the melting temperature of the backing material to drive off solvent.

It is to be understood that while the invention has been described in conjunction with the preferred specific embodiment thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

To fabricate a thin film of the backing material, any of the following methods can be used: cast film extrusion, blown-film extrusion, calendering and melt-compression. For this example, we heated the triblock copolymer, Kraton ® G-1650 (made by Shell Chemical Co.), between two metal plates, with a spacer of 0.004" thickness in between. The metal plates with the resin were brought into contact in a Carver Press (Carver, Inc., Menomonee Falls, Wis.) provided with a controllable heating and cooling arrangement. The temperature was kept at about 350° F. The sample was allowed to preheat for about 5 minutes without any applied pressure between the plates. The pressure was then raised in 5000 psi increments at 1 minute intervals, until it reached 20,000 psi. After 1 minute at 20,000 psi, the temperature was lowered by circulating cold water around the plates. After the plates had reached ambient temperature, the plates were removed and taken apart to yield a backing film of 0.005"±0.0005" thickness.

The tensile or Young's modulus of the film was measured as follows: a rectangular strip of width=0.5" and length=0.5" is cut out from the film using the appropriate die. This specimen is then clamped between the (pneumatic) jaws of an Instron Model 1011 Tensile Tester (Instron Corp., Canton, Mass.) This Instron uses Series IX Automated Material Testing Software (version 4.9); for our measurements, we employed Method G7, "Elastic Modulus Test". The jaws are pulled apart at 2"/min., and jaw separation is taken to be equal to the sample deformation. The force is recorded as a function of time, and the slope of the initial force−displacement curve (at 100% elongation) is converted to a modulus value using appropriate geometric factors, and quoted in dynes/cm².

The Moisture Vapor Transmission Rate (MVTR) is also measured using the ServoMed Evaporimeter EPID. A moist Kimwipe is used as the moisture source, and the sample is exposed to it through a circular hole made in a laminate consisting of sample, polyester and aluminum foil. The rate of evaporation, detected by the probe placed above the sample, is recorded on a strip chart recorder, as a function of time. Once the sample has attained equilibrium (the recorder trace levels off), the rate is recorded, in addition to the local relative humidity above the sample and the temperature. All rates are then normalized and reported as follows:

$$MVTR \text{ (normalized)} = MVTR \text{ (recorded)} \times (t/5) \times (50/(100-RH))$$

t = actual film thickness in mils
RH = local rel. humidity in %

The units are grams/m².hour For this material, the values of MVTR and Young's modulus were:

| Resin | MVTR (grams/m² · hour) | Modulus (dynes/cm²) |
|---|---|---|
| Kraton ® G-1650 | 0.40 | 17.0 × 10⁷ |

EXAMPLE 2

The drug/vehicle mixture is first dissolved or dispersed in the solution of the pressure-sensitive adhesive (PSA). To do this, the drug mixture is added to the PSA solution (usually in an organic solvent) and the mixture is kept stirred for about 8 hours. This mixture is then cast on to a release liner at the required thickness (typically 3 to 5 mils of dried adhesive) and dried in an oven at about 70° C. for 30 minutes. This adhesive/drug/vehicle mixture is brought into contact with the backing film and laminated at a pressure of about 100 psi using a rubber roller for a few minutes. The laminate backing film/adhesive/release liner is then cut into rectangular strips of 20 cm² area using a die-cutter. Such a patch, when stored at ambient temperature for several weeks, showed no swelling of the backing layer. Also, placebo patches made with the same adhesive composition, but without drug, when applied to human subjects, wore well for at least 4 to 5 days, without excessive wrinkling or delamination.

EXAMPLE 3

The procedure of Example 1 was followed, except for substitution of a C-Flex ® resin (Concept Technologies, Clearwater, Fla.) for the Kraton ® resin. The Carver press was kept at the same temperature, and the same molding procedure was followed. The values obtained for modulus and MVTR were:

| Resin | MVTR (grams/m² · hour) | Modulus (dynes/cm²) |
|---|---|---|
| C-Flex ® R70-006 | 1.0 | 3.0 × 10⁷ |

We claim:

1. An improved transdermal drug delivery device for administering a drug to a predetermined area of skin or mucosa, comprising a laminated composite which includes (a) a layer of a pressure-sensitive, pharmaceutically acceptable adhesive comprised of a material that is permeable to the drug, and which defines the basal surface of the device and adheres to the skin during use, and (b) a backing layer is substantially impermeable to the drug and which defines the upper surface of the device during use, wherein the improvement comprises:
   employing as the backing layer a single homogenous sheet of a thermoplastic or crosslinked elastomeric material having a moisture vapor transmission rate in the range of about 0.1 to 2 g/m²/hr and a Young's modulus in the range of about $10^4$ to about $10^9$ dynes/cm², and which is inert with respect to all components of the device.

2. The transdermal drug delivery device of claim 1, wherein the backing layer has a Young's modulus in the range of about $10^5$ to $10^8$ dynes/cm².

3. The transdermal drug delivery device of claim 1, wherein the elastomeric material is a thermoplastic elastomer selected from the group consisting of:
   (a) an A-B-A block copolymer;
   (b) a blend of an A-B-A block copolymer and a polyolefin;
   (c) a blend of an A-B-A block copolymer and poly(dimethyl siloxane);
   (d) high molecular weight poly(isobutylene);
   (e) a vulcanized mixture of ethylene-propylene diene rubber and polypropylene;
   (f) a vulcanized mixture of nitrile or natural rubber with polypropylene; and
   (g) mixtures thereof.

4. The transdermal drug delivery device of claim 3, wherein the thermoplastic elastomer is an A-B-A block copolymer wherein the A block is styrene and the B block is a saturated hydrocarbon.

5. The transdermal drug delivery device of claim 1, wherein the thermoplastic elastomer is a blend of a polyolefin and an A-B-A block copolymer wherein the A block is styrene and the B block is a saturated hydrocarbon.

6. The transdermal drug delivery device of claim 1, wherein the elastomeric material is a crosslinked elastomer selected from the group consisting of:
   (a) a vulcanized natural rubber;
   (b) a vulcanizable fluoroelastomer;
   (c) a blend of a vulcanized natural rubber with a polyolefin;
   (d) a blend of a vulcanizable fluoroelastomer with a polyolefin; and
   (e) mixtures thereof.

7. An improved method for administering a drug to a predetermined area of skin or mucosa which comprises placing a drug-containing laminated composite in drug-transmitting relationship to the skin, wherein the laminated composite includes (a) a layer of a pressure-sensitive, pharmaceutically acceptable adhesive comprised of a material that is permeable to the drug, and which defines the basal surface of the device and adheres to the skin during use, and (b) a backing layer that is substantially impermeable to the drug and which defines the upper surface of the device during use, wherein the improvement comprises:

employing as the backing layer a single homogenous sheet of a thermoplastic or crosslinked elastomeric material having a moisture vapor transmission rate in the range of about 0.1 to 2 g/m$^2$/hr and a Young's modulus in the range of about $10^4$ to about $10^9$ dynes/cm$^2$, and which is inert with respect to all components of the device.

8. The method of claim 7, wherein the backing layer has a Young's modulus in the range of about $10^5$ to $10^8$ dynes/cm$^2$.

9. The method of claim 7, wherein the elastomeric material is a thermoplastic elastomer selected from the group consisting of:
   (a) an A-B-A block copolymer;
   (b) a blend of an A-B-A block copolymer and a polyolefin;
   (c) a blend of an A-B-A block copolymer and poly(dimethyl siloxane);
   (d) high molecular weight poly(isobutylene);
   (e) a vulcanized mixture of ethylene-propylene diene rubber and polypropylene;
   (f) a vulcanized mixture of nitrile or natural rubber with polypropylene; and
   (g) mixtures thereof.

10. The method of claim 9, wherein the thermoplastic elastomer is an A-B-A block copolymer wherein the A block is styrene and the B block is a saturated hydrocarbon.

11. The method of claim 9, wherein the thermoplastic elastomer is a blend of a polyolefin and an A-B-A block copolymer wherein the A block is styrene and the B block is a saturated hydrocarbon.

12. The method of claim 7, wherein the elastomeric material is a crosslinked elastomer selected from the group consisting of:
   (a) a vulcanized natural rubber;
   (b) a vulcanizable fluoroelastomer;
   (c) a blend of a vulcanized natural rubber with a polyolefin;
   (d) a blend of a vulcanizable fluoroelastomer with a polyolefin; and
   (e) mixtures thereof.

13. An improved method for making a transdermal drug delivery device comprising laminating a pharmaceutically acceptable, pressure-sensitive adhesive layer to a backing layer which defines the upper surface of the device and is substantially impermeable to the drug, wherein the improvement comprises:

employing as the backing layer is a single homogenous sheet of a thermoplastic or crosslinked elastomeric material having a moisture vapor transmission rate in the range of about 0.1 to 2 g/m$^2$/hr and a Young's modulus in the range of about $10^4$ to about $10^9$ dynes/cm$^2$, and which is inert with respect to all components of the device.

14. The method of claim 13, wherein the backing layer has a Young's modulus in the range of about $10^5$ to $10^8$ dynes/cm$^2$.

15. The method of claim 13, wherein the elastomeric material is a thermoplastic elastomer selected from the group consisting of:
   (a) an A-B-A block copolymer;
   (b) A blend of an A-B-A block copolymer and a polyolefin:
   (c) a blend of an A-B-A block copolymer and poly(dimethyl siloxane);
   (d) high molecular weight poly(isobutylene);
   (e) a vulcanized mixture of ethylene-propylene diene rubber and polypropylene;
   (f) a vulcanized mixture of nitrile or natural rubber with polypropylene; and
   (g) mixtures thereof.

16. The method of claim 15, wherein the thermoplastic elastomer is an A-B-A block copolymer wherein the A block is styrene and the B block is a saturated hydrocarbon.

17. The method of claim 15, wherein the thermoplastic elastomer is a blend of a polyolefin and an A-B-A block copolymer wherein the A block is styrene and the B block is a saturated hydrocarbon.

18. The method of claim 14, wherein the elastomeric material is a crosslinked elastomer selected from the group consisting of:
   (a) a vulcanized natural rubber;
   (b) a vulcanizable fluoroelastomer;
   (c) a blend of a vulcanized natural rubber with a polyolefin;
   (d) a blend of a vulcanizable fluoroelastomer with a polyolefin; and
   (e) mixtures thereof.

* * * * *